(12) United States Patent
Ribble et al.

(10) Patent No.: US 7,385,802 B1
(45) Date of Patent: Jun. 10, 2008

(54) ELECTROLYTIC CAPACITOR

(75) Inventors: Bruce A. Ribble, Easley, SC (US);
Thomas T. Davis, Greenville, SC (US);
Wallace Ken Hall, Pickens, SC (US)

(73) Assignee: Pacesetter Inc., Sunnyvale, CA (US)

( * ) Notice: Subject to any disclaimer, the term of this patent is extended or adjusted under 35 U.S.C. 154(b) by 86 days.

(21) Appl. No.: 11/244,956

(22) Filed: Oct. 5, 2005

(51) Int. Cl.
*H01G 9/04* (2006.01)
*H01G 9/145* (2006.01)

(52) U.S. Cl. .................. 361/508; 361/528
(58) Field of Classification Search ........ 361/502–503, 361/508–509, 528–529
See application file for complete search history.

(56) References Cited

U.S. PATENT DOCUMENTS

| | | | | |
|---|---|---|---|---|
| 2,178,936 A | * | 11/1939 | Knab et al. | 361/510 |
| 4,518,471 A | | 5/1985 | Arora | 204/129.1 |
| 4,525,249 A | | 6/1985 | Arora | 204/129.75 |
| 4,671,858 A | * | 6/1987 | Kunugihara et al. | 205/87 |
| 4,827,381 A | * | 5/1989 | Brommer et al. | 361/531 |
| 4,831,490 A | * | 5/1989 | Voeten et al. | 361/523 |
| 5,131,388 A | | 7/1992 | Pless et al. | 128/419 D |
| 5,370,663 A | | 12/1994 | Lin | 607/5 |
| 5,496,481 A | | 3/1996 | Liu | 252/62.2 |
| 5,507,966 A | | 4/1996 | Liu | 252/62.2 |
| 5,522,851 A | | 6/1996 | Fayram | 607/5 |
| 5,584,890 A | * | 12/1996 | MacFarlane et al. | 29/25.03 |
| 5,687,057 A | | 11/1997 | Dapo | 361/506 |
| 5,715,133 A | | 2/1998 | Harrington et al. | 361/500 |
| 5,822,177 A | | 10/1998 | Popp et al. | 361/508 |
| 5,930,109 A | | 7/1999 | Fishler | 361/508 |
| 6,006,133 A | | 12/1999 | Lessar et al. | 607/5 |
| 6,110,233 A | | 8/2000 | O'Phelan et al. | 29/25.03 |
| 6,249,423 B1 | | 6/2001 | O'Phelan et al. | 361/502 |
| 6,493,212 B1 | | 12/2002 | Clarke et al. | 361/521 |
| 6,527,955 B1 | | 3/2003 | Sun | 210/555.22 |
| 6,587,329 B1 | | 7/2003 | Feger | 361/504 |
| 6,680,841 B2 | | 1/2004 | Tadanobu et al. | 361/523 |
| 6,765,784 B2 | * | 7/2004 | Ohya et al. | 361/523 |
| 6,799,072 B2 | | 9/2004 | Ries et al. | 607/36 |
| 6,819,544 B1 | | 11/2004 | Nielsen et al. | 361/508 |
| 6,881,232 B2 | | 4/2005 | O'Phelan et al. | 29/25.03 |
| 2002/0034062 A1 | | 3/2002 | O'Phelan et al. | 361/511 |
| 2004/0105212 A1 | | 6/2004 | O'Phelan et al. | 361/302 |
| 2004/0120099 A1 | | 6/2004 | Elliott et al. | 361/301.5 |
| 2005/0117277 A1 | | 6/2005 | Norton et al. | 361/512 |

FOREIGN PATENT DOCUMENTS

| | | |
|---|---|---|
| EP | 1 296 389 A1 | 9/2002 |
| GB | 2132019 A * | 6/1984 |
| JP | 6-208849 | 7/1994 |
| WO | WO 99/54896 | 10/1999 |
| WO | WO 99/59174 | 11/1999 |
| WO | WO 00/79550 A1 | 12/2000 |

* cited by examiner

*Primary Examiner*—Eric Thomas
(74) *Attorney, Agent, or Firm*—Steven M. Mitchell

(57) ABSTRACT

This disclosure provides folded anode assemblies, conjoined cathode assemblies, and flat stack capacitor configurations comprising such assemblies, and methods of preparing the various assemblies. The anode assemblies, conjoined cathode assemblies and capacitor configurations disclosed herein can be used in implantable cardioverter defibrillators.

8 Claims, 8 Drawing Sheets

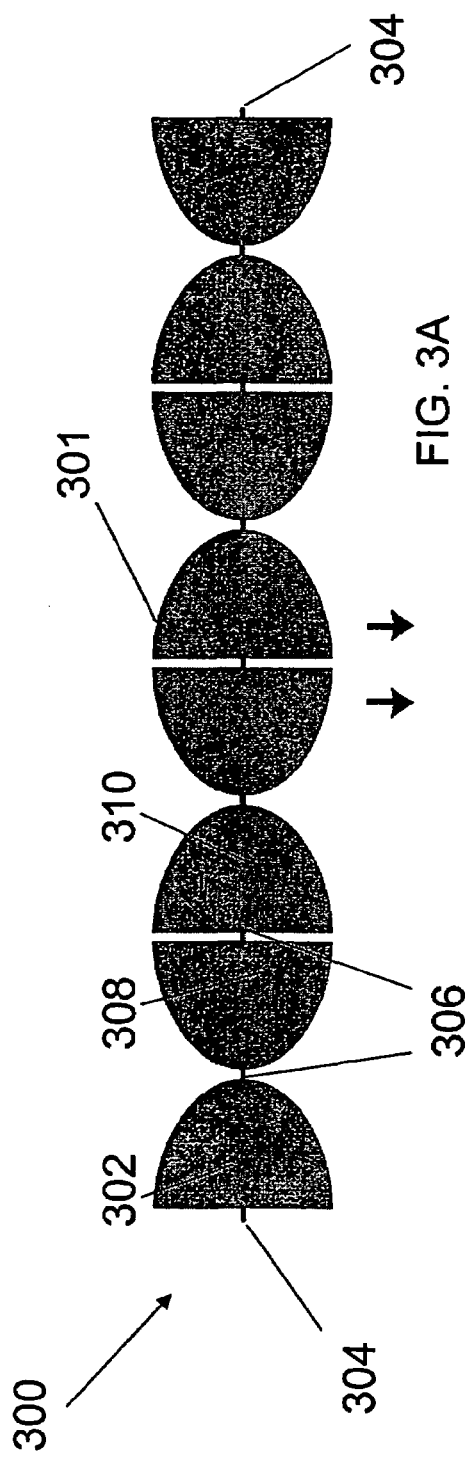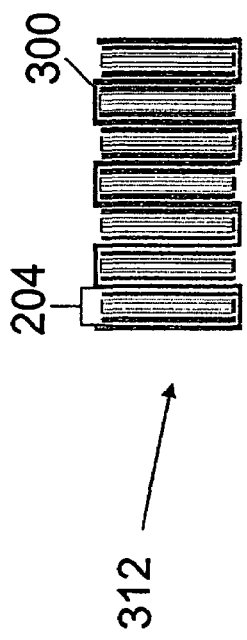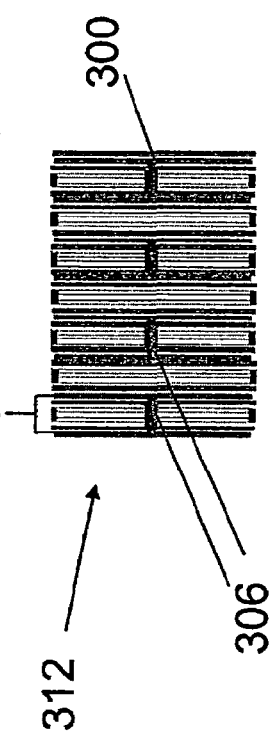

ELECTROLYTIC CAPACITOR

BACKGROUND OF THE INVENTION

1. Field of the Invention

Electrolytic capacitors and, more particularly, multiple anode stacked capacitor constructions comprising folded anode assemblies and/or conjoined capacitor assemblies for use with electrolytic capacitors are disclosed, as well as electrolytic capacitors comprising the anode assemblies and/or capacitor configurations.

2. Background of the Invention

Compact, high voltage capacitors are utilized as energy storage reservoirs in many applications, including implantable medical devices. These capacitors are required to have a high energy density since it is desirable to minimize the overall size of the implanted device. This is particularly true of an Implantable Cardioverter Defibrillator (ICD), also referred to as an implantable defibrillator, since the high voltage capacitors used to deliver the defibrillation pulse can occupy as much as one third of the ICD volume.

Implantable Cardioverter Defibrillators typically use two electrolytic capacitors in series to achieve the desired high voltage for shock delivery. For example, an implantable cardioverter defibrillator may utilize two 350 to 400 volt electrolytic capacitors in series to achieve a voltage of 700 to 800 volts.

Electrolytic capacitors are used in ICDs because they have the most nearly ideal properties in terms of size, reliability and ability to withstand relatively high voltage. Conventionally, such electrolytic capacitors typically consist of a cathode electrode, an electrically conductive electrolyte and a porous anode with a dielectric oxide film formed thereon. While aluminum is generally used for the anode plates, other metals such as tantalum, magnesium, titanium, niobium, zirconium and zinc may be used. Flat constructions for aluminum electrolytic capacitors are known, comprising a planar, layered, stack structure of electrode materials with separators interposed therebetween and connections between the various anode and cathode layers made via tabs on each individual electrode layer.

The need for high voltage, high energy density capacitors is most pronounced when employed in implantable cardiac defibrillators. Since the capacitance of an electrolytic capacitor is provided by the anodes, a clear strategy for increasing the energy density in the capacitor is to minimize the volume taken up by paper and cathode and maximize the number and volume of the anodes. For example, a multiple anode flat, stacked capacitor configuration requires fewer cathodes and paper spacers than a single anode configuration and thus reduces the size of the device. A multiple anode stack consists of a number of units consisting of a cathode, a paper spacer, two or more anodes, a paper spacer and a cathode, with neighboring units sharing the cathode between them. In order to achieve higher energy densities, three, four and five anodes can be stacked per layer. Maximization of the anode volume may also be accomplished by etching to achieve more effective anode surface area, and making the relative size of the anode plates larger with respect to the cathode plates.

Current multiple anode flat, stack capacitor configurations comprise on the order of 78 separate components (including anodes, cathodes and separator papers) which leads to substantial manufacturing time and cost, as well as labor intensive assembly processes. In addition, a significant portion (about 13%) of the capacitor volume is used to align the various components of the stack configurations (for example, through alignment holes) and to make the electric connections between the various parts (e.g., by tabs). This reduces the energy density of the capacitor and also increases the volume and mass of the ICD. There is, therefore, a need for improved methods and configurations that reduce the cost and time associated with flat capacitor manufacturing and assembly, while increasing the energy density and reducing the volume and mass of the capacitor configurations.

SUMMARY OF THE INVENTION

This disclosure provides anode assemblies, conjoined cathode assemblies, and flat, stack capacitor configurations comprising such assemblies, and methods of preparing the various assemblies that meet these various needs in the art.

In an embodiment, multiple layer anode assemblies are provided, comprising at least a first anode foil section and a second anode foil section, wherein the first section is folded onto the second section at least one foldable connection. The multiple anode assemblies can also be enclosed in separator materials, such as paper or polymeric materials.

Flat, stacked capacitor configurations, electrolytic capacitors and implantable cardiac defibrillators (ICD), comprising the various assemblies, are also disclosed, as well as process for preparing electrolytic capacitors comprising the various assemblies.

BRIEF DESCRIPTION OF THE DRAWINGS

FIGS. 3A-3C show a conjoined cathode assembly and a flat, stacked capacitor configuration.

DETAILED DESCRIPTION OF THE INVENTION

While specific configurations and arrangements are discussed, it should be understood that this is done for illustrative purposes only. A person skilled in the relevant art will recognize that other configurations and arrangements can be used. It will also be apparent to a person skilled in the relevant art that the various embodiments disclosed herein can be employed in a variety of other devices and applications.

It should be understood that the spatial descriptions (e.g., "above," "below," "up," "down," "top," "bottom," etc.) have their normal meanings in the art, and are used herein for purposes of illustration only, and that the embodiments disclosed herein can be spatially arranged in any orientation or manner.

Figure 1:
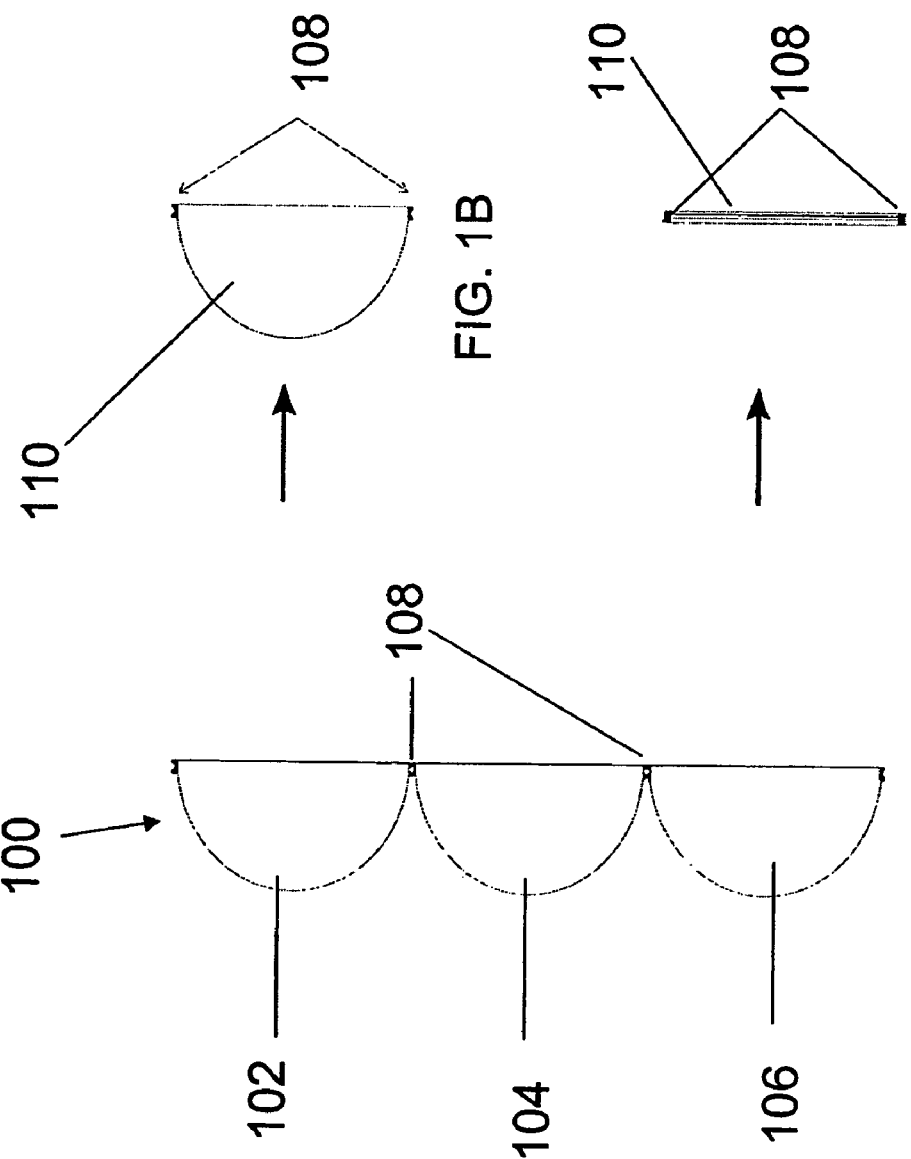
FIG. 1A shows an anode assembly.
FIG. 1B shows a top view of an anode assembly after folding.
FIG. 1C shows a side view of an anode assembly after folding.

FIG. 1A shows a flat anode foil 100 having first 102, second 104 and third 106 sections. Anode foils disclosed throughout can be produced by any suitable method, such as laser cutting, dye cutting and the like. First 102 and second 104 sections, and second 104 and third 106 sections of anode foil 100 are shown connected by at least one foldable connection 108. While FIG. 1A shows only a single foldable connection between sections of the anode foil, any number of foldable connections between the various sections can be used. As used herein, the term "foldable connection," as it relates to anode assemblies, is used to indicate a portion of the anode foil that provides electrical connectivity between the various anode foil sections and yet is flexible enough to be folded such that the various sections of the anode foil can be folded onto one another. Foldable connections 108 shown in FIGS. 1A, 1B and 1C are shown as small portions of anode foil 100 connecting the various sections (102, 104, 106) and further include a circular shaped hole punched or cut therethrough. As shown in FIG. 1B, when sections 102, 104 and 106 of anode foil 100 are folded upon one another, the anode foil 100 is folded at approximately the bisection point of the circular shape hole punched or cut therein. Thus, in the resulting configuration, as shown in FIG. 1B, foldable connections 108 are shown with a half-circle shaped cut out. Foldable connections 108 can be prepared by cutting and removing surrounding anode foil material such that a single (as shown), or multiple, foldable connections are created between the various sections (102, 104, 106) of anode foil 100. Preferably, foldable connections 108 are cut (e.g., dye cut) from the same piece of foil material 100 as the various anode foil sections 102, 104, 106, and thus, foldable connections 108 and the various anode foil sections 102, 104, 106 form a single, continuous piece of material. In other embodiments, foldable connections 108 can be produced from a separate piece(s) of material and then attached to the various anode foil sections. In other embodiments, foldable connections 108 can simply be a portion of anode foil 100 that can be folded so as to allow the various anode foil sections, 102, 104, 106, to fold upon one another. That is, foldable connections 108 can simply be a region at which the anode foil 100 is folded, and can comprise any shape or dimension relative to the various anode foil sections.

FIG. 1B shows a top view (i.e., looking at the top surface of section 102) of the multiple layer anode assembly 110 after it has been folded. FIG. 1C shows a side view (i.e., looking at the edge of all three anode foil sections) of the multiple layer anode assembly 110 after it has been folded. The anode assembly can be folded in any manner. For example, multiple layer anode assembly 110 can be prepared by folding section 106 onto section 104 at foldable connection 108, such that the top of section 106 (side facing outward in FIG. 1A) is folded onto, and thus comes in contact with (or in direct proximity with), the top of section 104 (side facing outward in FIG. 1A). Sections 104 and 106 can then be folded under section 102 at foldable connection 108, such that the bottom of section 104 (side facing away in FIG. 1A) is folded under, and thus comes in contact with (or in direct proximity with), the bottom of section 102 (side facing away in FIG. 1A). After the three anode foil sections are folded in such a manner, folded multiple layer anode assembly 110 is produced. As shown in FIG. 1C, folded anode assembly will suitably be substantially flat comprising the various sections folded onto one another. As used herein, the term "substantially flat" is used to mean that the anode foil sections, or other components of the various stacked capacitor assemblies disclosed herein, are brought in close proximity with one another in a planar orientation such that the surfaces of the various components touch, or nearly touch. Anode foil sections 102, 104 and 106 are folded such that each foil section contacts the adjacent foil section (or is in direct proximity with the adjacent foil section) to produce a folded multiple layer anode assembly 110 that is compact, and as shown in FIG. 1B, has flat area dimensions that are only as large as a single anode foil section; and has thickness dimensions that are approximately the same thickness as the separate anode foil sections (or slightly larger allowing a small amount of space between the adjacent sections). As used herein, the terms "anode assembly," "folded anode assembly," "multiple layer anode assembly" and "folded multiple layer anode assembly" are used interchangeably.

Sections 102, 104 and 106 of anode foil 100 are shown as half-circle shaped sections of foil. Anode foils can be produced by any suitable method, such as laser cutting, dye cutting and the like. While any suitable shape can be used, half-circle shaped foil sections provide for a maximum area of anode foil for use in an electrolytic capacitor housing (see description below). The shapes of anode foil sections 102, 104 and 106, however, can be modified by those skilled in the art to work with other configurations or capacitor housings, for example, circular, square, rectangular, triangular and the like.

As shown in FIG. 1A, foldable connections 108 suitably connect the sections of anode foil 100 at the corners of the half-circular shaped sections (102, 104, 106). However, foldable connections 108 can be positioned at any suitable location on sections 102, 104 and 106. Alternative positions include any where along the arc of the half-circular shape, or at any position along the flat bottom section of the half-circular shape. In addition, multiple foldable connections 108 (e.g., 2, 3, 4, 5, 10, etc.) can be placed between the various sections 102, 104, 106 of anode foil 100. In other embodiments, a foldable connection 108 can run along the entire length of the flat portion of the half-circle shaped sections, thus allowing folding along the base of the sections. Generally, foldable connections 108 will be produced from the same piece of anode foil 100 material from which the various anode foil sections 102, 104, 106, were produced. While FIG. 1A shows an anode foil 100 with three sections, anode foils comprising any number of sections can be used in the anode assemblies and flat, stacked capacitor configurations described herein. For example, anode foil 100 can comprise 2, 3, 4, 5, 10, 15, 20, etc. sections. The use of half-circle shapes at the foldable connection facilitates assembly and alignment. After stacking, electrical connection of the folded anode assemblies 110 are made to a pin or wire (see below). The pin or wire readily fits into the half-circle shape at the fold. The use of a cylindrically shaped pin or wire is a very consistent and cost effective method for connecting the anodes subassemblies.

Flat anode foil 100 can comprise any suitable material known in the art for use in electrolytic capacitors. Aluminum foil is one example of a material for use as anode foil 100 because of its ability to produce a sufficient quality oxide layer, its conductive properties, and its wide commercial availability. Other metal foils conventionally utilized in electrolytic capacitors may also be used, including titanium, tantalum, magnesium, niobium, zirconium and/or zinc. For example, a strip of unetched, high purity (99.99%) aluminum foil with high cubicity, wherein at least 85% of the crystalline aluminum structure is oriented in a normal position (i.e., a (1,0,0) orientation) relative to the surface of the foil, can be used. Such foils are well-known in the art and are readily available from commercial sources.

In another embodiment, anode foil 100 may be etched to increase surface area, such as in an aqueous halide based etch solution, typically a hydrochloric acid or sodium chloride solution, according to a conventional etch process. For example, U.S. Pat. No. 5,715,133 to Harrington et al. describes a suitable method of etching foil, the disclosure of which is incorporated herein by reference in its entirety. The etch solution can consist of about 1.3% by weight sodium chloride, about 3.5% by weight sodium perchlorate, about 0.35% sodium persulfate, and deionized water. The etch solution is heated to a temperature in the range of about 60° C. to about 95° C. The foil is etched at a DC current density of about 0.01 A/cm$^2$ to about 0.30 A/cm$^2$. A charge of about 20 coulombs/cm$^2$ to 100 coulombs/cm$^2$ is passed through the foil during the etching process, which requires an etch time in the range of about 2 minutes to about 12 minutes. In order to protect foldable connections 108 from the etching process which can weaken the connections, making them brittle and difficult to fold, an etch mask can be layered over foldable connections 108 to protect them. Thus, when etching takes place, foldable connections 108 will not be etched, or will be less etched than the remainder of the foil. Etch masks that can be used to protect foldable connections 108 are well known in the art. While etching can either occur prior to or after the anode foil sections 102, 104, 106 are folded, suitably, etching will occur prior to folding the various sections to produce folded anode assembly 110.

The etched foil is then removed from the etch solution and rinsed in deionized water. The tunnels formed during the initial etch are then widened, or enlarged, in a secondary etch solution, typically in an aqueous based nitrate solution between about 1% to about 20% aluminum nitrate, or between about 10% to about 14% aluminum nitrate, with less than about 1% free nitric acid. The etch tunnels are widened to an appropriate diameter by methods known to those in the art, such as those disclosed in U.S. Pat. No. 4,518,471 and U.S. Pat. No. 4,525,249, both of which are incorporated herein by reference.

After the etch tunnels have been widened, the foil is again rinsed with deionized water and dried. Finally, a barrier oxide layer is formed onto one or both surfaces of the metal foil by placing the foil into an electrolyte bath and applying a positive voltage to the metal foil and a negative voltage to the electrolyte. The barrier oxide layer provides a high resistance to current passing between the electrolyte and the metal foils in the finished capacitor, also referred to as the leakage current. A high leakage current can result in the poor performance and reliability of an electrolytic capacitor. In particular, a high leakage current results in a greater amount of charge leaking out of the capacitor once it has been charged.

The formation process may consist of applying a voltage to the foil through an electrolyte such as boric acid and water or other solutions familiar to those skilled in the art, resulting in the formation of an oxide on the surface of the anode foil. An example electrolyte for formation is a 100-1000 µS/cm, e.g., 500 µS/cm, citric acid concentration. In the case of an aluminum anode foil, the formation process results in the formation of aluminum oxide ($Al_2O_3$) on the surface of the anode foil. The thickness of the oxide deposited or "formed" on the anode foil is proportional to the applied voltage, roughly 10 to 15 Angstroms per applied volt.

The etched, widened and formed anode foil 100 can then be folded as discussed above to produce folded anode assembly 110 (or may be folded prior to etching and widening).

Figure 2:
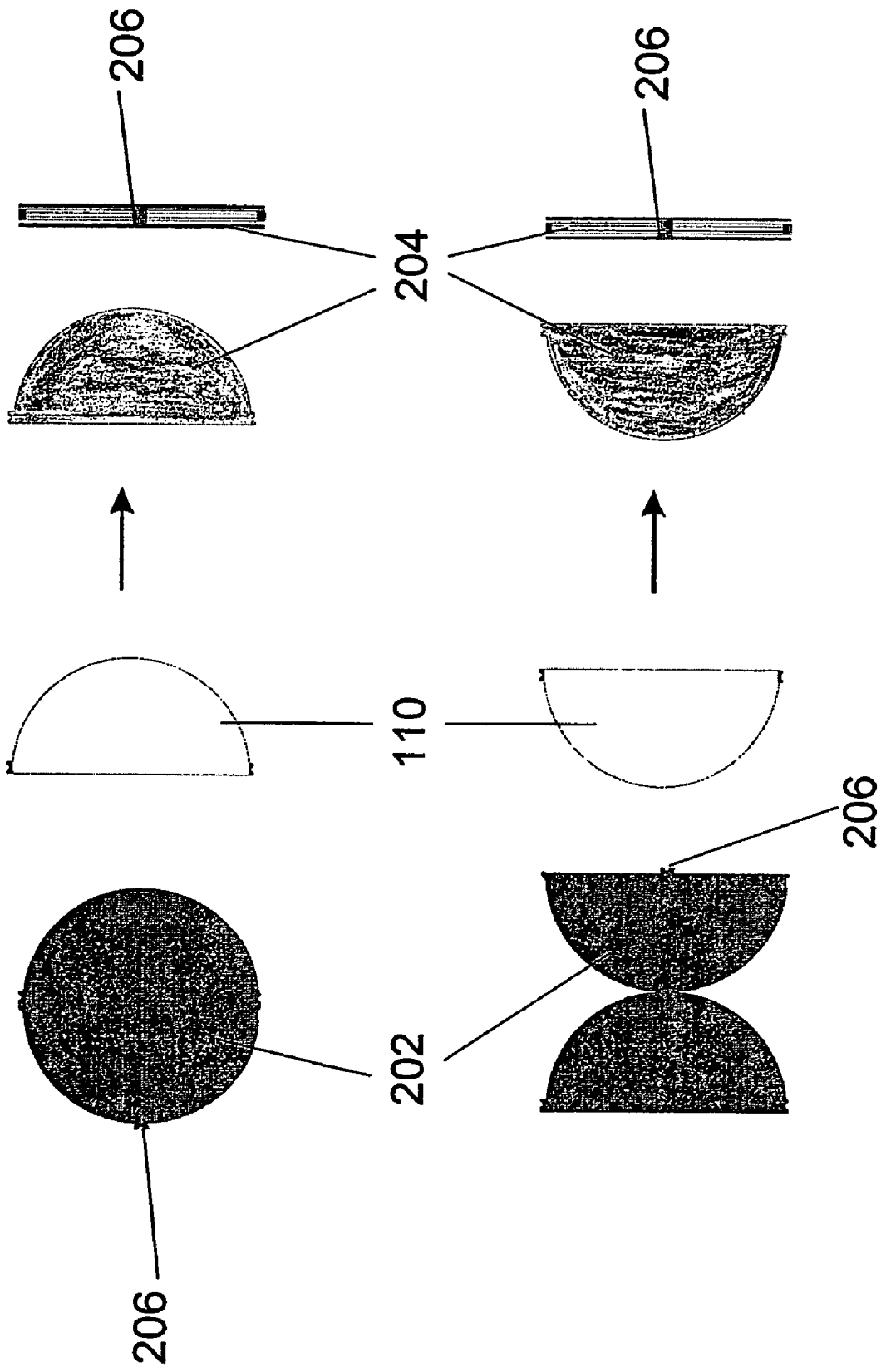
FIG. 2 shows a process for the enclosure of a folded anode assembly.

Anode assembly 110 may also be enclosed in a separator material 202, such that separator material 202 prevents direct contact between folded anode assembly 100 and an adjacent cathode when folded anode assembly 110 is placed in an electrolytic capacitor. As shown in FIG. 2, separator material 202 can comprise a single piece of material that is cut (e.g., dye cut, laser cut and the like) so as to fold over anode assembly 110 to produce enclosed anode assembly 204. While two separate, unconnected pieces of separator material 202 can be used to enclose anode assembly 110, use of a single piece of separator material 202 reduces the total number of components required to produce a flat, stacked capacitor configuration. As shown in FIG. 2, separator material 202 is folded over anode assembly 110 such that both exposed, flat sides of anode assembly 110 are covered by a layer of separator material in the resulting enclosed anode assembly 204. In the example embodiment in FIG. 2, enclosed anode assembly 204 comprises an anode assembly 110 with three anode foil sections folded together and then enclosed in separator material 202. However, it should be understood that any number of anode foil sections can be used to generate enclosed anode assembly 204.

Materials utilized as separator material 202 should be permeable to ions so as to allow dissolved ions in an electrolyte solution to pass through the materials and contact the surface of the anode foils, thereby carrying current between the anode foils and a cathode. Separator material 202 provides the separation layer required to insulate the anodes from both adjacent cathodes, and the metallic surface of the surrounding housing or case used in a stacked capacitor configuration.

Example materials that can be used as separator material 202 include, but are not limited to, polymeric materials and paper. For example, paper such as Kraft paper, can be used as separator material 202. Polymeric materials that can be used as separator material 202 include, but are not limited to, polypropylene (PP), polyethylene (PE), polypropylene-polyethylene copolymers (e.g. PP/PE/PP), polyimides, polyamide imides, polyether imides, polysulfones, polyether sulfones, polyaryl sulfones, polyether ketones, polyether ether ketones, polyphenylene sulfides and polyarylates. Additional polymeric materials include those discussed in U.S. Pat. No. 6,527,955, incorporated herein by reference in its entirety. In example embodiments, the polymeric materials utilized as separator materials can be polyethylene (e.g. TONEN® 25, available from Tonen Corp., Japan) or polyethylene-polypropylene copolymers (e.g. CELGARD® 2300 (PP/PE/PP) and CELGARD® 4560, available from Celgard LLC, Charlotte, N.C.) as discussed in European Patent Application EP 1 296 389, the disclosure of which is incorporated herein by reference in its entirety.

FIG. 3A shows a conjoined cathode assembly 300, comprising a flat, cathode foil 301 having a first cathode foil section 302, a second cathode foil section 308 and a third cathode foil section 310 (as well as additional cathode foil sections, as shown, also conjoined). Cathode foils can be produced from any suitable material, such as conductive metals, e.g., aluminum and titanium. Cathode foils disclosed throughout can be produced by any suitable method, such as laser cutting, dye cutting and the like. As used herein, the term "conjoined" is used to indicate that the various sections of cathode assembly 300 are joined or connected together such that the cathode assembly is electrically connected such as to act as one cathode. The terms "conjoined cathode assembly," "conjoined cathode" and "cathode assembly" are used herein interchangeably. First section 302 of conjoined cathode assembly 300 is connected to second section 308 by foldable connection 306. As used herein, the term "foldable connection," as it relates to cathode assemblies, is used to indicate a portion of cathode foil 301 that provides electrical connectivity between the various cathode foil sections and is flexible enough to be folded, such that the various sections of the cathode foil can be folded onto one another and/or around anode foils and/or anode assemblies 204. Foldable connection 306 can be prepared by cutting and removing surrounding cathode foil material such that a single, (as shown) or multiple, foldable connections are created between the various sections (302, 308, 310) of conjoined cathode assembly 300. In other embodiments, foldable connection 306 may not be prepared by cutting and removing cathode foil material, but can simply be a portion of the cathode foil that can be folded so as to allow the various sections to fold around an anode assembly. While a single foldable connection 306 is shown between each cathode section, multiple foldable connections of any size and shape can be used. Preparing foldable connection 306 out of the same material as the sections of conjoined cathode assembly 300 allows each separate section (302, 308, 310) to be electrically connected to each other section, such that conjoined cathode 300 acts as if it were a single cathode. Cathode connection 304 allows conjoined cathode assembly 300 to be electrically connected to a cathode source, such as the top and/or bottom of an electrolytic capacitor housing. Conjoined cathode assembly 300 can consist of any number of connected sections, e.g., 2, 3, 4, 5, 6, 7, 8, 9, 10, 15, 20, 25, 30, 50, etc.

Conjoined cathode assembly 300 is designed such that first section 302 and second section 308 are folded at foldable connection 306 over or around at least one anode foil, such that the anode foil is disposed on both sides by a section of cathode foil. As used herein, the terms "disposed" and "disposed adjacent" are used to mean that the anode and cathode foils (or other assembly components as appropriate) are arranged next to each other such that the metallic films are capable of acting as capacitors. The terms "disposed," "disposed adjacent" and "layered" are all used interchangeable herein. For example, an anode foil can be disposed on the top surface (surface facing up in FIG. 3A) of second cathode foil section 308. Preferably, the anode foil will be covered or encapsulated by a separator material to prevent direct contact between the anode foil and the cathode foil. Cathode assembly 300 is then folded at foldable connection 306 such that the top surface (surface facing up in FIG. 3A) of first cathode foil section 302 is disposed on one side of an anode foil and the top surface (surface facing up in FIG. 3) of second foil section 308 is disposed on the other side of the anode foil thus creating a "sandwiching" of the anode foil between two cathode foil sections (i.e., an anode foil between two cathode foils). A second anode foil can then be disposed adjacent the bottom surface (surface facing down in FIG. 3A) of second section 308 and a third cathode foil section 310 can then be folded at foldable connection 306 such that the bottom surface (surface facing down in FIG. 3A) of section 310 is disposed adjacent the second anode foil.

While any suitable shape can be used, half-circle shaped cathode foil sections provide for a maximum area of cathode foil to be placed in an electrolytic capacitor housing (see below) and also match the shape of the anode foil sections. The shapes of cathode foil sections 302, 308 and 310, however, can be modified by those skilled in the art to work with other configurations or capacitor housings, such as circular, square, rectangular, triangular and the like. As shown in FIG. 3A, in one embodiment, foldable connections 306 connect adjacent, conjoined cathode foil sections (302, 308, 310) at the top and base of the half-circle shaped sections. Other points of connection between the various sections of conjoined cathode assembly 300, e.g. at the corners of the half-circle shape, or at any point along the half-circle shape, can also be used.

While a single anode foil can be used in conjunction with conjoined cathode assembly 300, generally more than one anode foil will be placed between conjoined cathode foil sections. For example, in a flat, stacked capacitor configuration, several anode foils (e.g., 2, 3, 4, 5, 6, 7, 8, 9, 10, etc.) can be placed between connected sections of conjoined cathode assembly 300, generally with separator materials separating the cathode foils from the anode foils. The conjoined cathode assembly 300 can also be used in conjunction with anode assembly 110 and enclosed anode assembly 204 discussed above. When anode assembly 110 is used, separator material may be placed between anode assembly 110 and the sections of cathode assembly 300 so as to not allow direct contact between the anode and cathode foils. When enclosed anode assembly 204 is used, additional separator material is not required (but can be used) and the enclosed anode assembly 204 is placed between adjacent sections of conjoined cathode assembly 300. Conjoined cathode assembly 300 is then folded at foldable connections 306 such that conjoined cathode assembly 300 forms a serpentine configuration as shown in FIG. 3B, where enclosed anode assemblies 204 are sandwiched between two cathode foil sections, one on either side of the enclosed anode assembly 204, to form flat, stacked capacitor configuration 312. As shown in FIG. 3B, looking at the side of flat, stacked capacitor configuration 312 (i.e., the edges of the anode and cathode foils), conjoined cathode assembly 300 is folded in such a way that it weaves back and forth in between enclosed anode assemblies 204. As shown in FIG. 3C, looking down at the top of the assembly, foldable connections 306 are visible connecting the sections of conjoined cathode 300, and traverse the edges of enclosed anode assembly 204. Separation tab 206, shown in FIG. 2, provides separation between the foil edges of anode assembly 110, and foldable connections 306 of the surrounding cathode sections. Separation tabs 206 are not shown in FIG. 3C, but lie between the metal of foldable connections 306 and the edges of enclosed anode assembly 204 in order to keep the two metallic materials from touching. In other embodiments, the enclosed anode assemblies 204 can be used in conjunction with separate, non-conjoined cathode sections, e.g., 308, 310. In such embodiments, the enclosed anode assembly 204 is disposed adjacent non-conjoined cathode sections which are then later electrically connected.

Enclosed anode assemblies 204 and conjoined cathode assemblies 300 disclosed herein can be used to create electrolytic capacitors. Suitably, such electrolytic capacitors are constructed by stacking a plurality of enclosed anode assemblies 204 with a conjoined cathode assembly 300 folded around the enclosed anode assemblies 204 in a serpentine fashion to create flat, stacked capacitor configuration 312. The enclosed anode assemblies 204 may comprise a plurality of anode foil sections folded and stacked together to form a high energy density anode element, for example 3 or more anode foil sections. The enclosed anode assemblies 204 are then disposed adjacent a cathode, but due to the presence of the separator material, the anodes and cathode do not themselves contact. An electrolytic capacitor can be prepared by stacking a plurality of units comprising a conjoined cathode assembly 300 and enclosed anode assemblies 204 comprising 2, 3, 4, 5, 6, 7, 8, etc. connected anode foils folded upon one-another and enclosed in separator material. Suitably, several enclosed anode assemblies 204 will be used to prepare the stacked capacitor configurations 312. The anode assemblies 204 and cathode assembly 300 are then connected together in a parallel connection to produce sufficient capacitance for the intended function. This finished stack can then be inserted into a case with a geometry closely following the contour of the stack, and designed to minimize the space occupied inside the finished defibrillator.

Figure 4B:
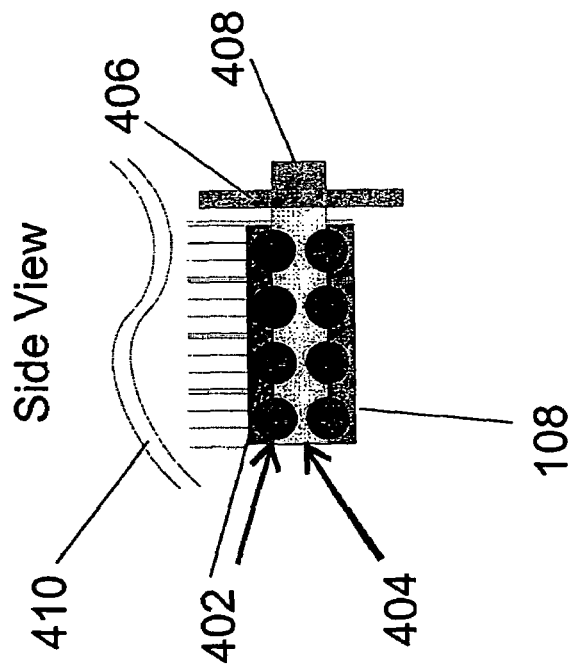
FIGS. 4A and B show electrical connection of a capacitor sub-assembly.
Figure 4A:
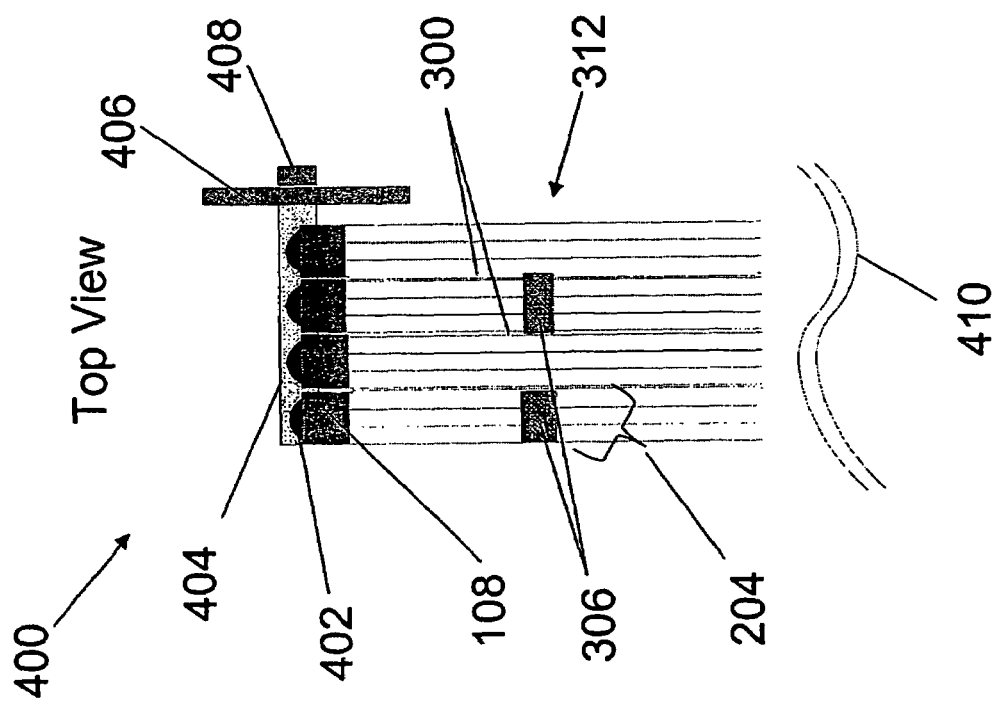

The anode assemblies 110, enclosed anode assemblies 204, conjoined cathode assemblies 300, and flat, stacked capacitor configuration 312 described throughout can be used to form capacitor sub-assemblies 400. FIGS. 4A and 4B illustrate capacitor sub-assembly 400 in which the components of flat, stacked capacitor configuration 312 are electrically connected together. FIG. 4A shows a top view (looking down at the top of anode assemblies 204) of flat, stacked capacitor configuration 312 connected to a pin 404 via laser spot welds 402. The upper portions of foldable connections 108, i.e. the upper portions of the half-circular cut-outs, are visible. Generally, pin 404 will be a circular-shaped metallic connection pin made of any suitable material, such as aluminum or similar materials. Pin 404 is connected to a flange 406 and a laser spot weld connection 408 that can be used to connect the capacitor sub-assembly 400 to an electrolytic capacitor housing, for example. Laser spot welds 402 are made between each foldable connection 108 and pin 404. FIG. 4B shows a side view of capacitor sub-assembly 400, i.e., looking at the side edges of flat, stacked capacitor configuration 312. Both the top and bottom portions of foldable connection 108 are visible, as foldable connection 108, after it has been folded, forms a half-circle shaped void where pin 404 (suitably circular shaped) will fit and thus provide an electrical connection. Laser spot welds 402 connect pin 404 to each portion of foldable connection 108. Cathode connection wire 410 is shown in both FIGS. 4A and 4B simply to illustrate that it can also be present in capacitor sub-assembly 400 to provide electrical connection for conjoined cathode 300. Capacitor sub-assembly 400 can then be placed in an electrolytic capacitor housing and ultimately in an ICD. While sub-assembly 400 shows only 4 enclosed anode assemblies 204, it should be understood that any number of enclosed anode assemblies 204, e.g., 2, 3, 4, 5, 6, 7, 8, 9, 10, 15, 20, etc., can be used to create capacitor sub-assemblies 400.

Figure 5:
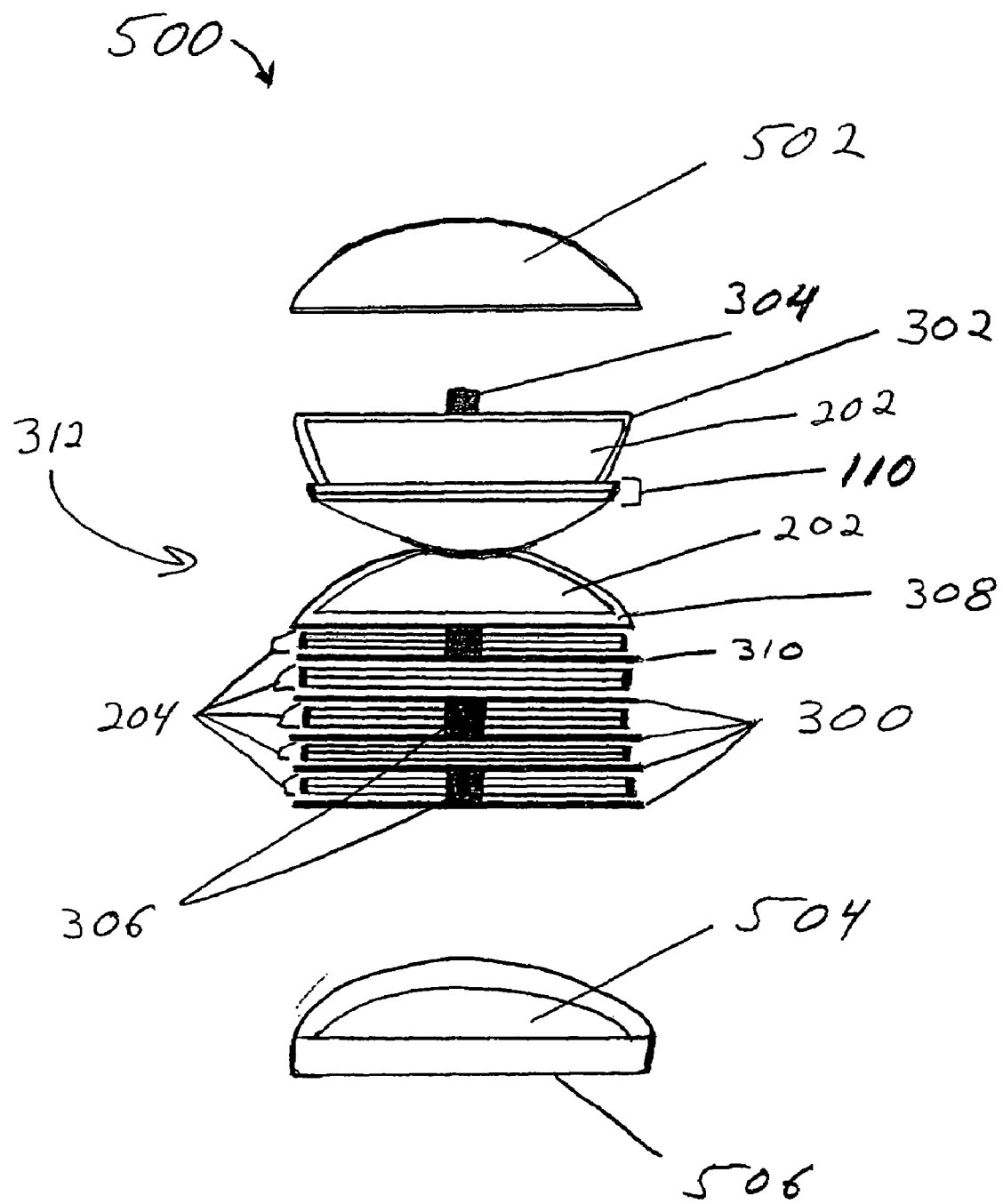
FIG. 5 shows an electrolytic capacitor having a multiple anode flat, stacked capacitor configuration utilizing a folded anode assembly.

FIG. 5 illustrates a capacitor 500 having a multiple anode flat, stacked capacitor configuration. Capacitor 500 consists of flat, stacked capacitor configuration 312 within a housing 506 enclosed by a lid 502. The dielectric can be provided by an oxide layer on the etched surface of the anode assemblies 110, while the conjoined cathode assembly 300 includes the conductive cathode sections 302, 308, 310. An electrolyte-saturated separator material 202 encloses the folded anode assembly 110 and electrolyte fills the tunnels on the surface of the anodes. Each of the sections, e.g., 302, 308, 310 of conjoined cathode assembly 300 is connected together with a foldable connection 306, to allow for electrical interconnection, and conjoined cathode 300 has a cathode connection 304, for electrical connection, suitably to the bottom of housing 506 and/or to lid 502. Each of the anode assemblies 204 are connected together, for example as shown in capacitor sub-assembly 400 in FIGS. 4A and 4B, to achieve electrical interconnection. The illustration in FIG. 5 shows each enclosed anode 204 assembly having three anode foil sections per assembly, for example, although, there may be one or more anode foils per assembly, e.g. 2, 3, 4, 5, 6, 7, 8, etc. Additionally, one or both of the end cathodes may be removed, with the housing 506 or lid 502, themselves connected to the other cathodes and functioning as a cathode. While capacitor 500 is shown comprising six enclosed anode assemblies 204, capacitor 500 can comprise any number of enclosed anode assemblies, e.g., 2, 3, 4, 5, 6, 7, 8, 9, 10, 11, 12, 13, 14, 15 or more. In other embodiments, multiple anode flat, stacked capacitor configurations can utilize enclosed anode assemblies 204 in combination with traditional, non-conjoined cathodes. Similarly, the conjoined cathode assemblies 300 disclosed herein can be used with individual anode foils to generate flat, stacked capacitor configurations.

Housing 506 can be an aluminum, stainless steel, plastic, or other suitable material container that defines a chamber 504 in which the flat, stacked capacitor configuration 312 is closely received. Chamber 504 preferably has a depth equal to the thickness of the stack, but may be of any desired configuration. The enclosed anode assemblies 204 can be welded together and electrically connected to pin 404, for example, as shown in capacitor sub-assembly 400 in FIGS. 4A and 4B. Conjoined capacitor configuration 300 can also be electrically connected to housing 506 and/or lid 502 or other suitable electrical connection.

A Kraft paper or porous polymeric spacer as disclosed herein may act as the separator material to prevent electrical contact between the flat anodes and cathode sheets. An electrolytic capacitor 500 generally comprises at least one stacked unit consisting of: a conjoined cathode assembly 300, at least one anode assembly 110 and a separator material 202 (i.e., at least one enclosed anode assembly 204), with neighboring anode assemblies 110 sharing the cathode section (e.g., 302, 308, 310) between them. Suitably, the capacitor configuration comprises a conjoined cathode assembly 300, and 2, 3, 4, 5, 6, 7, 8, 9, 10, 11, 12, 13, 14, 15, etc. enclosed anode assemblies 204. The conjoined cathode assembly 300 is then folded around the individual, enclosed anode assemblies 204 in a serpentine fashion, and then the entire flat, stacked capacitor configuration 312 is placed in a housing 506 (suitably with a lid 502) to generate an electrolytic capacitor 500.

In embodiments discussed above, the pre-assembled capacitor is then vacuum impregnated with an electrically conductive electrolyte, by placing the capacitor in contact with the electrolyte and reducing the pressure to less than 50 cm Hg. The capacitor electrolyte is typically ethylene glycol based with a straight chain dicarboxlyic acid and/or boric acid. Other suitable electrolytes include those known to the ordinarily skilled artisan, including those disclosed in U.S. Pat. No. 5,496,481 to Liu, U.S. Pat. No. 5,507,966 to Liu, U.S. Pat. No. 5,687,057 to Dapo and U.S. Pat. No. 6,587,329 to Feger, the disclosures of each of which are incorporated by reference herein in their entireties. The electrolyte is neutralized with ammonia or an amine and a cathode depolarizer, typically a nitro-aromatic compound such as nitrobenzene, nitroacetophenone, or nitroanisole, may be added to the electrolyte to improve the gas evolution behavior of the titanium cathode. Suitably, a cathode depolarizer is added in the range of about 0 to about 5% by weight. For example, a cathode depolarizer will be added at about 1% by weight. The capacitor is held at this low pressure for 5 to 45 minutes and then pressure is restored, using the pressure to force the electrolyte mixture into the capacitor stack. The capacitor is then removed and placed in an oven at a temperature of about 65° C. to about 90° C. and a maximum oxygen atmospheric concentration of 2% for a period of about 2 hours to about 24 hours. The capacitor is then aged in a normal manner by applying the working voltage to the capacitor, allowing the capacitor to reach this voltage, and then allowing the current to decrease.

Electrolytic capacitors described throughout can be incorporated into implantable medical devices, such as implantable cardioverter defibrillators (ICDs), as would be apparent to one skilled in the art, as described in U.S. Pat. No. 5,522,851, incorporated by reference herein in its entirety.

Figure 6:
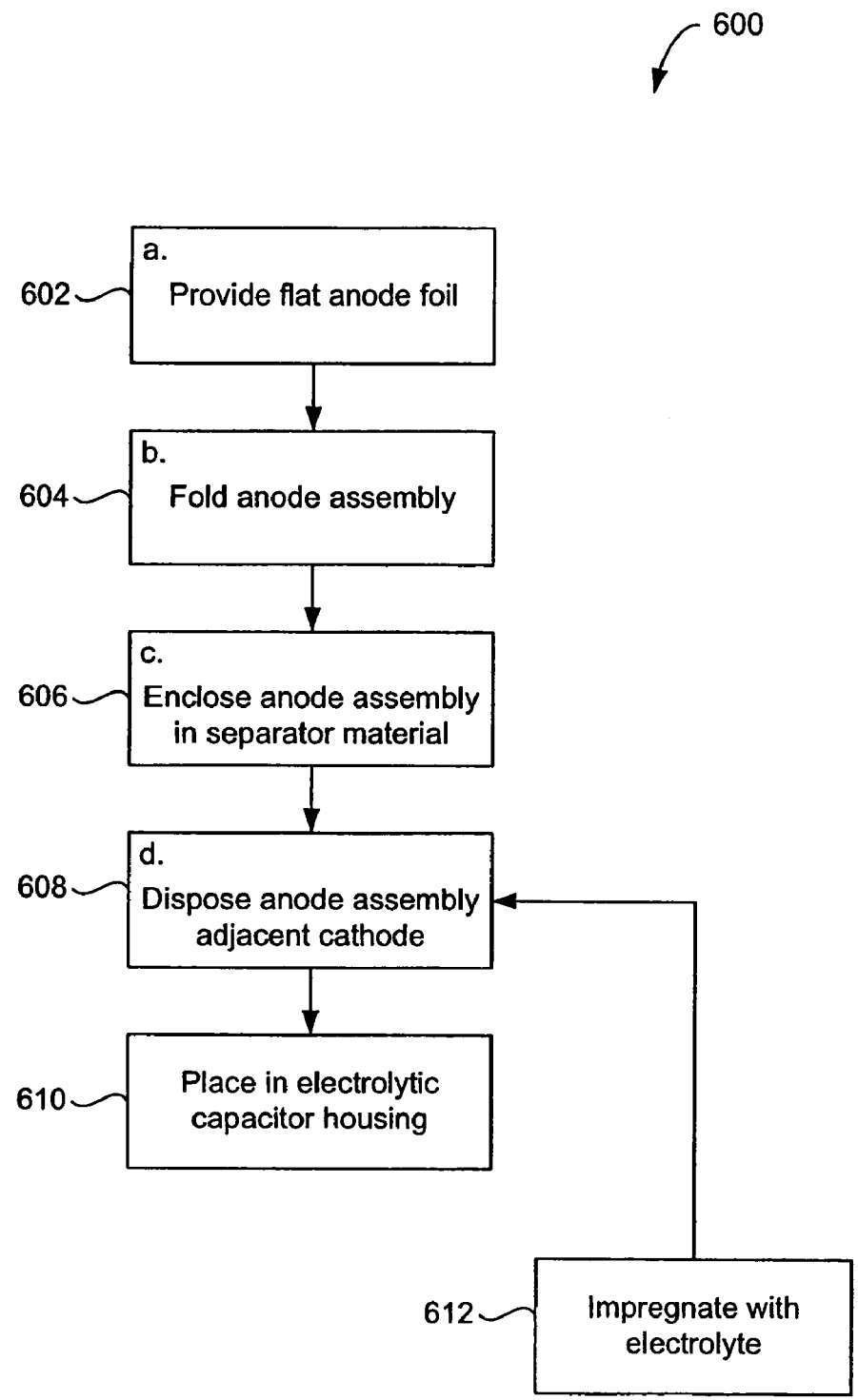
FIG. 6 shows a flowchart of a process for preparing an electrolytic capacitor utilizing a folded anode assembly and a conjoined cathode assembly.

Flowchart 600 of FIG. 6 illustrates a process for preparing an electrolytic capacitor, with reference to FIGS. 1A, 1B, 2 and 3A-3C. In step 602 of FIG. 6, a flat anode foil 100 having at least a first section 102, and a second section 104, at least one foldable connection 108 between the first 102 and second 104 sections, such as shown in FIG. 1A is provided. In step 604 of FIG. 6, the first section 102 is folded on top of the second section 104 at foldable connection 108, to produce a folded anode assembly 110, such as shown in FIG. 1B (e.g., the anode sections are folded flat on top of one another). In step 606 of FIG. 6, the folded anode assembly 110 is enclosed in a separator material 202, such as is shown in FIG. 2. In step 608 of FIG. 6, the enclosed anode assembly 204 is disposed adjacent at least one cathode, such as is shown in FIG. 3C. The various materials for the anode foils, cathode foils and separator materials described throughout can be used in any of the processes disclosed herein. As shown in FIG. 6, the process illustrated in flowchart 600 can further comprise step 610, placing the electrolytic capacitor in an electrolytic capacitor housing, such as shown in FIG. 5. The process illustrated in flowchart 600 can also further comprise step 612, impregnating the electrolytic capacitor with an ethylene glycol based electrolyte.

Figure 7A:
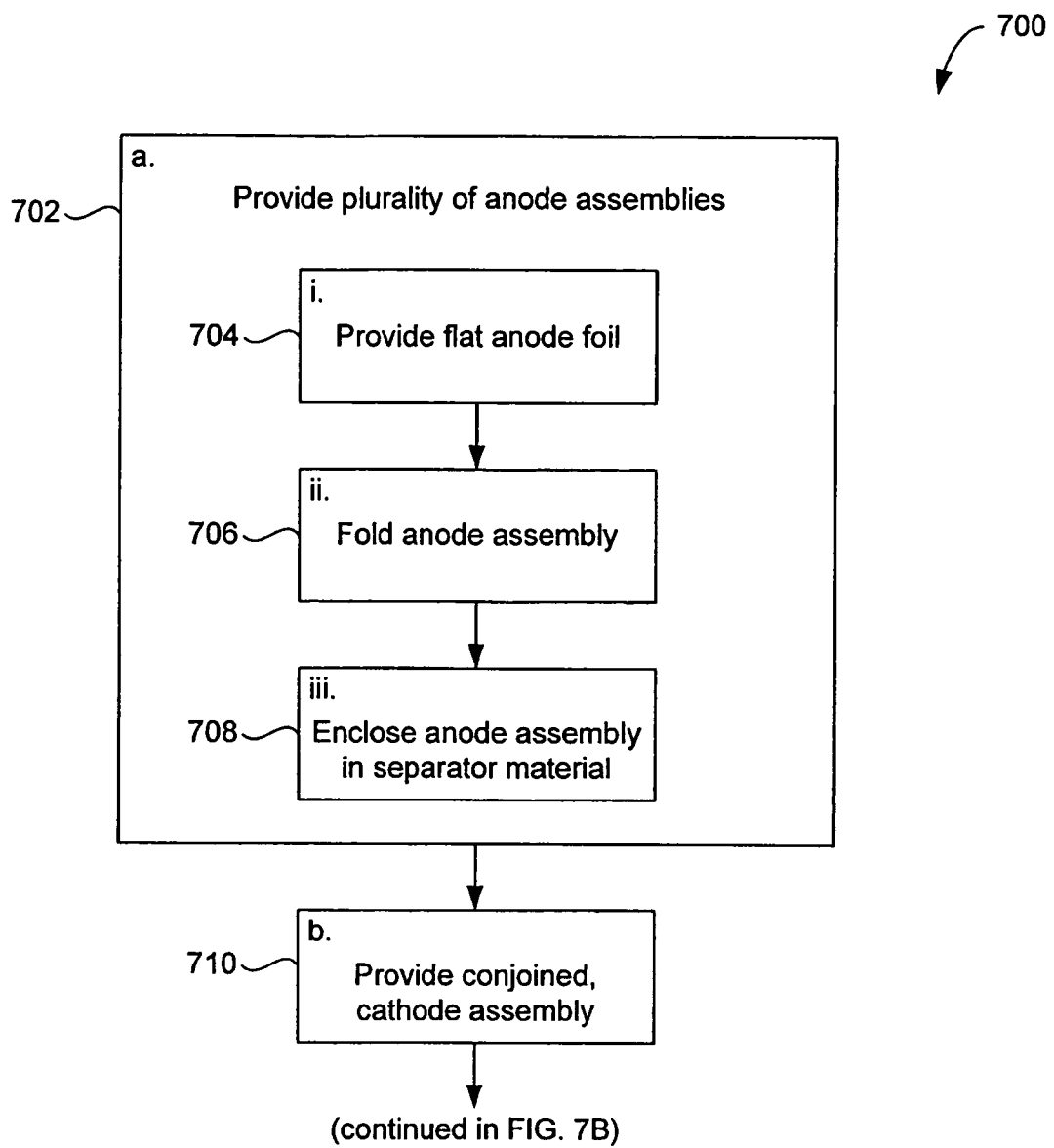
FIGS. 7A and 7B show a flowchart of a process for preparing an electrolytic capacitor utilizing a folded anode assembly and a conjoined cathode assembly.
Figure 7B:
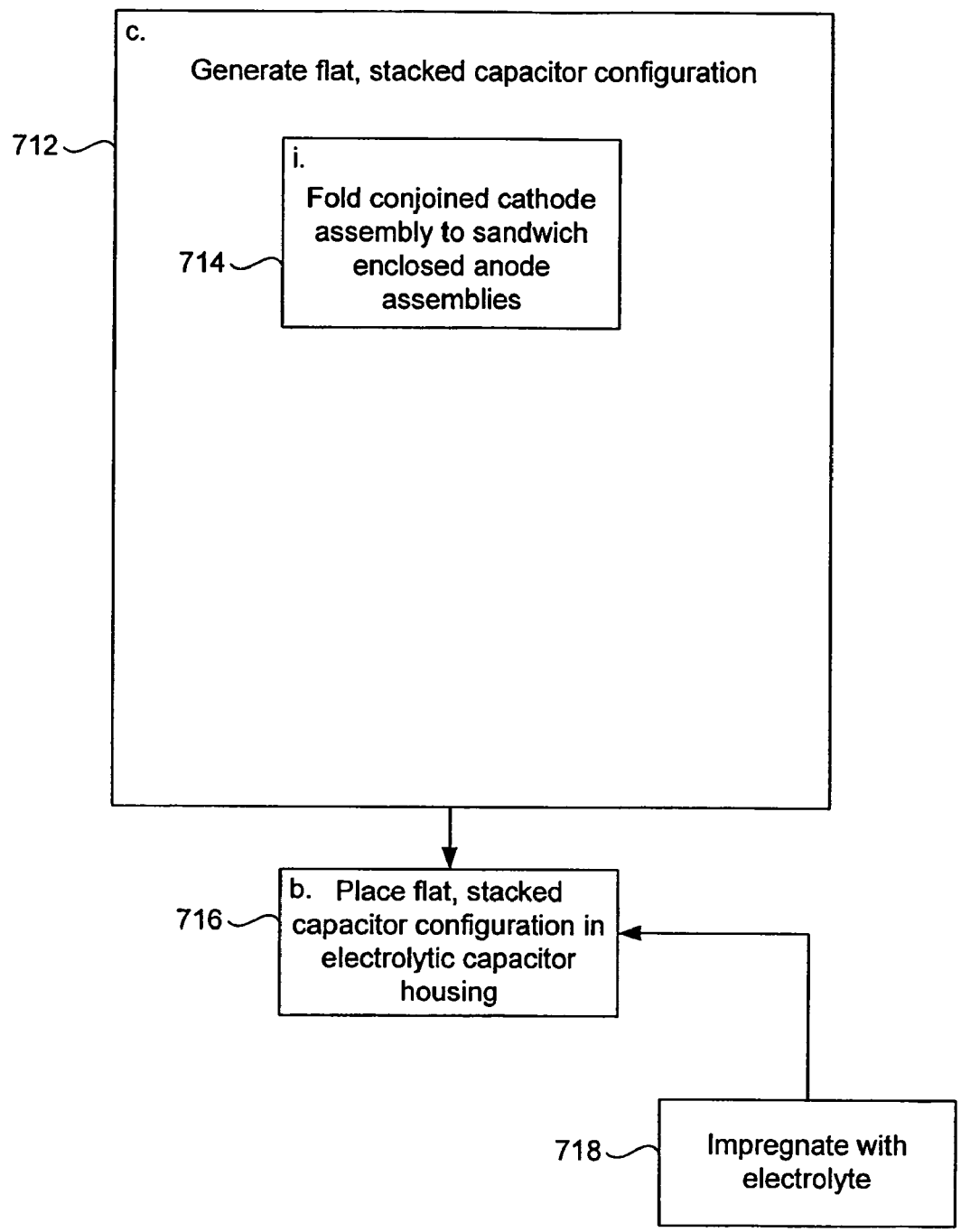

Flowchart 700 of FIGS. 7A and 7B illustrates a process for preparing an electrolytic capacitor 500, with reference to FIGS. 1A, 1B, 2, 3A-3C and 5. In step 702 of FIG. 7A, a plurality of enclosed anode assemblies 204 are produced, comprising: step 704 of FIG. 7A, providing a flat anode foil 100 having at least three sections 102, 104 and 106 and at least one foldable connection 108 between each section, such as is shown in FIG. 1A; step 706 of FIG. 7A, folding the three sections, 102, 104 and 106 on top of each other to produce a folded anode assembly 110, such as is shown in FIG. 1B; and step 708 of FIG. 7A, enclosing the folded anode assembly 110 in a separator material 202 to produce an enclosed anode assembly 204, such as is shown in FIG. 2. In step 710 of FIG. 7A, a conjoined cathode assembly 300 comprising a flat cathode foil having a plurality of conjoined cathode sections, 302, 308, 310, with at least one foldable connection 306 between each of the conjoined cathode sections, such as is shown in FIG. 3A is provided. In step 712 of FIG. 7B, a flat stacked capacitor configuration 312 is generated, comprising: step 714 of FIG. 7B, folding the conjoined cathode assembly 300 at each foldable connection 306 such that each of the enclose anode assemblies 204 is sandwiched between two adjacent conjoined cathode sections (e.g., 302 and 308, or 308 and 310), wherein the separator material 202 prevents the anode assemblies 110 from contacting the conjoined cathode sections, 302, 308, 310, such as is shown in FIGS. 3B and 5. In step 716 of FIG. 7B, the flat stacked capacitor configuration 312 is placed in an electrolytic capacitor housing 506 such that the housing provides cathode connections at either end of the capacitor 500 as shown in FIG. 5. Flowchart 700 of FIG. 7B can also further comprise step 718, impregnating the electrolytic capacitor 500 with an ethylene glycol based electrolyte. In another embodiment, lid 502 and housing 506 can provide the final cathode sections for capacitor 500, and thus, the processes can further comprise layering a enclosed anode assembly on both ends of stacked capacitor configuration 312.

While various embodiments have been described above, it should be understood that they have been presented by way of example only, and not limitation. Thus, the breadth and scope of this disclosure should not be limited by any of the above-described exemplary embodiments, but should be defined only in accordance with the following claims and their equivalents. Additionally, all references cited herein, including journal articles or abstracts, published or corresponding U.S. or foreign patent applications, issued U.S. or foreign patents, or any other references, are each entirely incorporated by reference herein, including all data, tables, figures, and text presented in the cited references.

The foregoing description of the specific embodiments will so fully reveal the general nature of the embodiments that others can, by applying knowledge within the skill of the art (including the contents of the references cited herein), readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A flat, stacked capacitor configuration, comprising:
   a multiple layer anode assembly, comprising an anode foil having at least a first section and a second section, wherein said first section is folded onto said second section at least one first foldable connection; and
   at least one cathode,
   wherein said at least one cathode is disposed adjacent said multiple layer anode assembly.

2. The flat, stacked capacitor configuration of claim 1, further comprising a separator disposed between said multiple layer anode assembly and said at least one cathode.

3. The flat, stacked capacitor configuration of claim 1, wherein said at least one cathode is a conjoined cathode assembly, comprising:
   a cathode foil having at least a first section and a second section; and
   at least one foldable connection between said first and second sections of said cathode foil,
   wherein said first and second sections of said cathode foil are folded over said multiple layer anode assembly, such that said multiple layer anode assembly is disposed between said first section of said cathode foil and said second section of said cathode foil.

4. The flat, stacked capacitor configuration of claim 3, further comprising:
   a second multiple layer anode assembly comprising an anode foil having at least a first section, and a second section, wherein said first section and said second section are folded onto one another at least one foldable connection, wherein said cathode foil further comprises a third section and said conjoined cathode assembly further comprises at least one foldable connection between said second section and said third section of said cathode foil, wherein said second multiple layer anode assembly is disposed between said second section of said cathode foil and said third section of said cathode foil.

5. An electrolytic capacitor comprising the flat, stacked capacitor configuration of claim 1.

6. An implantable cardiac defibrillator (ICD), comprising the electrolytic capacitor of claim 5.

7. A multiple layer anode assembly, comprising an anode foil having at least a first section and a second section, wherein said first section is folded onto said second section at least one first foldable connection, wherein said first and second sections are etched and wherein said foldable connection is not etched.

8. A flat, stacked capacitor configuration, comprising:

a multiple layer anode assembly, comprising an anode foil having at least a first section and a second section, wherein said first section is folded onto said second section at least one first foldable connection; and at least one cathode, wherein said at least one cathode is disposed adjacent said multiple layer anode assembly and wherein said multiple layer anode assembly is enclosed in a separator material.

* * * * *